United States Patent
Northen et al.

(10) Patent No.: US 11,964,972 B2
(45) Date of Patent: Apr. 23, 2024

(54) SALT FORM

(71) Applicant: CRT Pioneer Fund LP, Berkhamsted (GB)

(72) Inventors: Julian S. Northen, Sunderland (GB); John Mykytiuk, Sunderland (GB); Gillian Moore, Sunderland (GB)

(73) Assignee: CRT Pioneer Fund LP, Berkhamsted (GB)

( * ) Notice: Subject to any disclaimer, the term of this patent is extended or adjusted under 35 U.S.C. 154(b) by 655 days.

(21) Appl. No.: 15/734,145

(22) PCT Filed: Jun. 6, 2019

(86) PCT No.: PCT/GB2019/051574
§ 371 (c)(1),
(2) Date: Dec. 1, 2020

(87) PCT Pub. No.: WO2019/234435
PCT Pub. Date: Dec. 12, 2019

(65) Prior Publication Data
US 2021/0214350 A1    Jul. 15, 2021

(30) Foreign Application Priority Data
Jun. 8, 2018 (GB) .................................... 1809460

(51) Int. Cl.
*C07D 471/04* (2006.01)
(52) U.S. Cl.
CPC ........ *C07D 471/04* (2013.01); *C07B 2200/13* (2013.01)
(58) Field of Classification Search
CPC ............................ C07D 471/04; C07B 2200/13
See application file for complete search history.

(56) References Cited

U.S. PATENT DOCUMENTS

2021/0214350 A1    7/2021    Northen et al.

FOREIGN PATENT DOCUMENTS

| RU | 2007135053 A | 3/2009 | |
| RU | 2441869 C2 | 2/2012 | |
| RU | 2016137789 A | 4/2018 | |
| WO | WO-2014/037750 A1 | 3/2014 | |
| WO | WO-2014037750 A1 * | 3/2014 | ......... A61K 31/4375 |

OTHER PUBLICATIONS

Bastin et al., "Salt selection and Optimisation Procedures for Pharmaceutical New Chemical Entities," Organic Process Research and Development 4: pp. 427-435 (2000).
Caira., "Crystalline polymorphism of organic compounds," Topics in Current Chemistry, Springer Verlag Berlin Heidelberg, 198: pp. 163-208 (1998).
Stahl et al., "Handbook of Pharmaceutical Salts: Properties, Selection, and Use," International Union of Pure and Applied Chemistry, pp. 331-345.
Translation of Russian Search Report for PCT/GB2019/051572 dated Nov. 21, 2022.
International Search Report and Written Opinion for International Application No. PCT/GB19/51574 dated Jul. 30, 2019.

* cited by examiner

*Primary Examiner* — Sun Jae Yoo
(74) *Attorney, Agent, or Firm* — Foley Hoag LLP; David P. Halstead; Lawrence P. Tardibono

(57) ABSTRACT

Ditosylate salts of N2-(2-ethoxy-4-(4-methyl-4H-1,2,4-triazol-3-yl)phenyl)-6-methyl-N8-neopentylpyrido[3,4-d]pyrimidine-2,8-diamine, and crystalline forms thereof; processes for the preparation of the new salt forms; and their use as therapeutic agents for the treatment and/or prevention of proliferative diseases, such as cancer.

17 Claims, 8 Drawing Sheets

SALT FORM

RELATED APPLICATIONS

This application is the National Stage of International Patent Application No. PCT/GB2019/051574, filed Jun. 6, 2019, which claims the benefit of Great Britain Patent Application No. 1809460.7, filed Jun. 8, 2018. The contents of the International Patent Application are incorporated herein by reference in their entirety.

INTRODUCTION

The present invention relates to ditosylate salts of N2-(2-ethoxy-4-(4-methyl-4H-1,2,4-triazol-3-yl)phenyl)-6-methyl-N8-neopentylpyrido[3,4-d]pyrimidine-2,8-diamine, and crystalline forms thereof. The present invention also relates to processes for the preparation of the new salt forms and their use as therapeutic agents for the treatment and/or prevention of proliferative diseases, such as cancer.

BACKGROUND OF THE INVENTION

WO 2014/037750 describes N2-(2-ethoxy-4-(4-methyl-4H-1,2,4-triazol-3-yl)phenyl)-6-methyl-N8-neopentylpyrido[3,4-d]pyrimidine-2,8-diamine (see compound I, below) as an inhibitor of MPS1 kinase.

Compound I

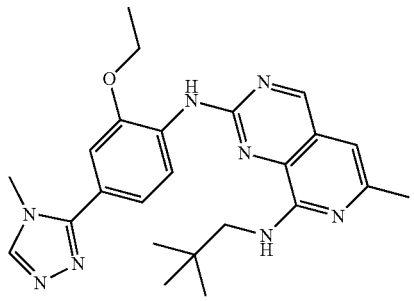

Studies have demonstrated that compound I exhibits potent MPS1 kinase inhibitory activity and thus can be expected to have therapeutic application in the treatment of proliferative disorders, such as cancer.

The present invention seeks to provide compound I in an alternative salt form. In particular, the invention seeks to provide a salt form of compound I that retains the desired pharmacological activity and demonstrates one or more advantageous properties.

An important solid state property of a pharmaceutical compound is its rate and extent of dissolution in aqueous fluid, particularly the digestive fluid of a subject. The rate of dissolution of an active ingredient in a subject's digestive fluid can have therapeutic consequences since it imposes an upper limit on the rate at which an orally-administered active ingredient can reach the subject's bloodstream.

Another important solid state property of a pharmaceutical compound is its storage stability or its tendency to absorb water from the surrounding environment, e.g. the air (i.e. hygroscopicity).

Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch, or tribasic calcium phosphate. The solid state form of a compound may also affect its behaviour on compaction.

These physicochemical characteristics and others may be influenced by salt form and/or the conformation and orientation of molecules in the unit cell, which defines a particular polymorphic form of a substance.

A polymorphic form may give rise to thermal behaviour different from that of the amorphous material or another polymorphic form. Thermal behaviour is measured in the laboratory by such techniques as capillary melting point, thermogravimetric analysis (TGA) and differential scanning calorimetric (DSC) and can be used to distinguish some polymorphic forms from others. It is important that a given therapeutic agent is polymorphically stable as changes in polymorphic form can lead to changes in physicochemical properties which may result in altered pharmacokinetics.

The solid forms of the present invention suitably have one or more advantageous features which may, but not exclusively, be selected from the properties mentioned above.

SUMMARY OF THE INVENTION

In one aspect, the present invention provides a ditosylate salt of a compound of formula I:

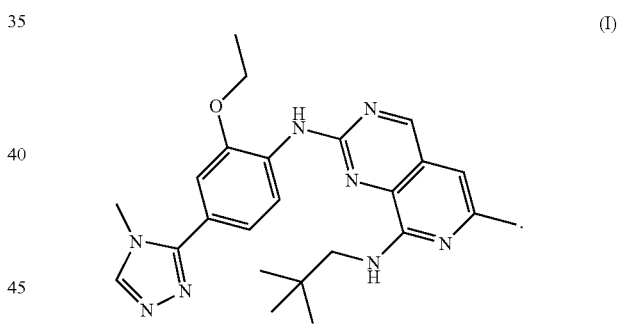

In another aspect, the present invention provides a pharmaceutical composition which comprises a ditosylate salt of a compound of formula I as defined herein and one or more pharmaceutically acceptable excipients.

In another aspect, the present invention provides a ditosylate salt of a compound of formula I as defined herein, or a pharmaceutical composition as defined herein, for use in therapy.

In another aspect, the present invention provides a ditosylate salt of a compound of formula I as defined herein, for use in the treatment of a proliferative disorder.

In another aspect, the present invention provides a ditosylate salt of a compound of formula I as defined herein, for use in the treatment of a cancer.

In another aspect, the present invention provides the use of a ditosylate salt of a compound of formula I as defined herein, in the manufacture of a medicament for the treatment of a proliferative disorder.

In another aspect, the present invention provides the use of a ditosylate salt of a compound of formula I as defined herein, in the manufacture of a medicament for the treatment of a cancer.

In another aspect, the present invention provides a method of treating a proliferative disorder, said method comprising administering to a subject in need thereof an effective amount of a ditosylate salt of a compound of formula I as defined herein.

In another aspect, the present invention provides a method of treating a cancer, said method comprising administering to a subject in need thereof an effective amount of a ditosylate salt of a compound of formula I as defined herein.

In another aspect, the present invention provides a combination comprising a ditosylate salt of a compound of formula I, as defined herein, with one or more additional therapeutic agents.

In another aspect, the present invention provides a process for the preparation of a ditosylate salt of a compound of formula (I) comprising adding para-toluenesulfonic acid to a solution of the compound of formula I in a mixture of an organic solvent and water, wherein the organic solvent is selected from acetone, 2-butanone and 2-propanol Preferred, suitable, and optional features of any one particular aspect of the present invention are also preferred, suitable, and optional features of any other aspect.

DETAILED DESCRIPTION OF THE INVENTION

In one aspect, the present invention relates to a ditosylate salt of the compound of formula I:

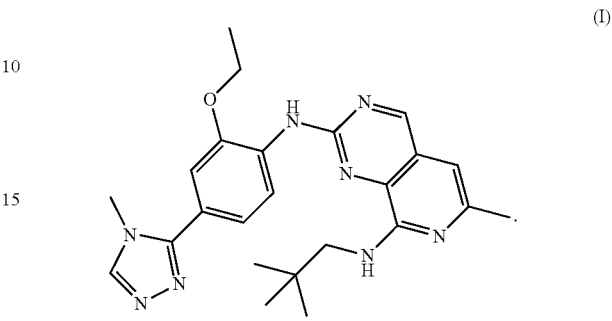

In one embodiment, the ditosylate salt of the compound of formula I is crystalline. Suitably, the ditosylate salt of a compound of formula I is in crystalline Form A.

Suitably the ditosylate salt of the compound of formula I is substantially polymorphically pure Form A, i.e. contains about 20% or less of any other polymorphic forms of the compound of formula I. Suitably, the ditosylate salt of the compound of formula I contains about 15% or less of any other polymorphic forms of the compound of formula I. Suitably, the ditosylate salt of the compound of formula I contains about 10% or less of any other polymorphic forms of the compound of formula I. Suitably, the ditosylate salt of the compound of formula I contains about 5% or less of any other polymorphic forms of the compound of formula I. Suitably, the ditosylate salt of the compound of formula I contains about 3% or less of any other polymorphic forms of the compound of formula I. Suitably, the ditosylate salt of the compound of formula I contains about 2% or less of any other polymorphic forms of the compound of formula I. Suitably, the ditosylate salt of the compound of formula I contains about 1% or less of any other polymorphic forms of the compound of formula I.

In one embodiment, the crystalline ditosylate salt of the compound of formula I may be characterised by X-ray powder diffraction (also referred herein as powder XRD, or PXRD, or XRPD). Suitably the X-ray powder diffraction patterns may be obtained using Cu Kα radiation (45 KV, 40 mA, 1.54 Å). Suitably, the XRPD patterns are acquired under ambient conditions. Suitably the data collection range is about 2 to about 35 degrees two-theta (° 2θ). Suitably, a continuous scan speed of about 0.2 degrees per second (°s⁻¹) is employed.

In one embodiment, the X-ray powder diffraction pattern is obtainable on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection is suitably X'Pert Data Collector, version 2.2f and the data suitably presented using X'Pert Data Viewer, version 1.2d.

Figure 1:
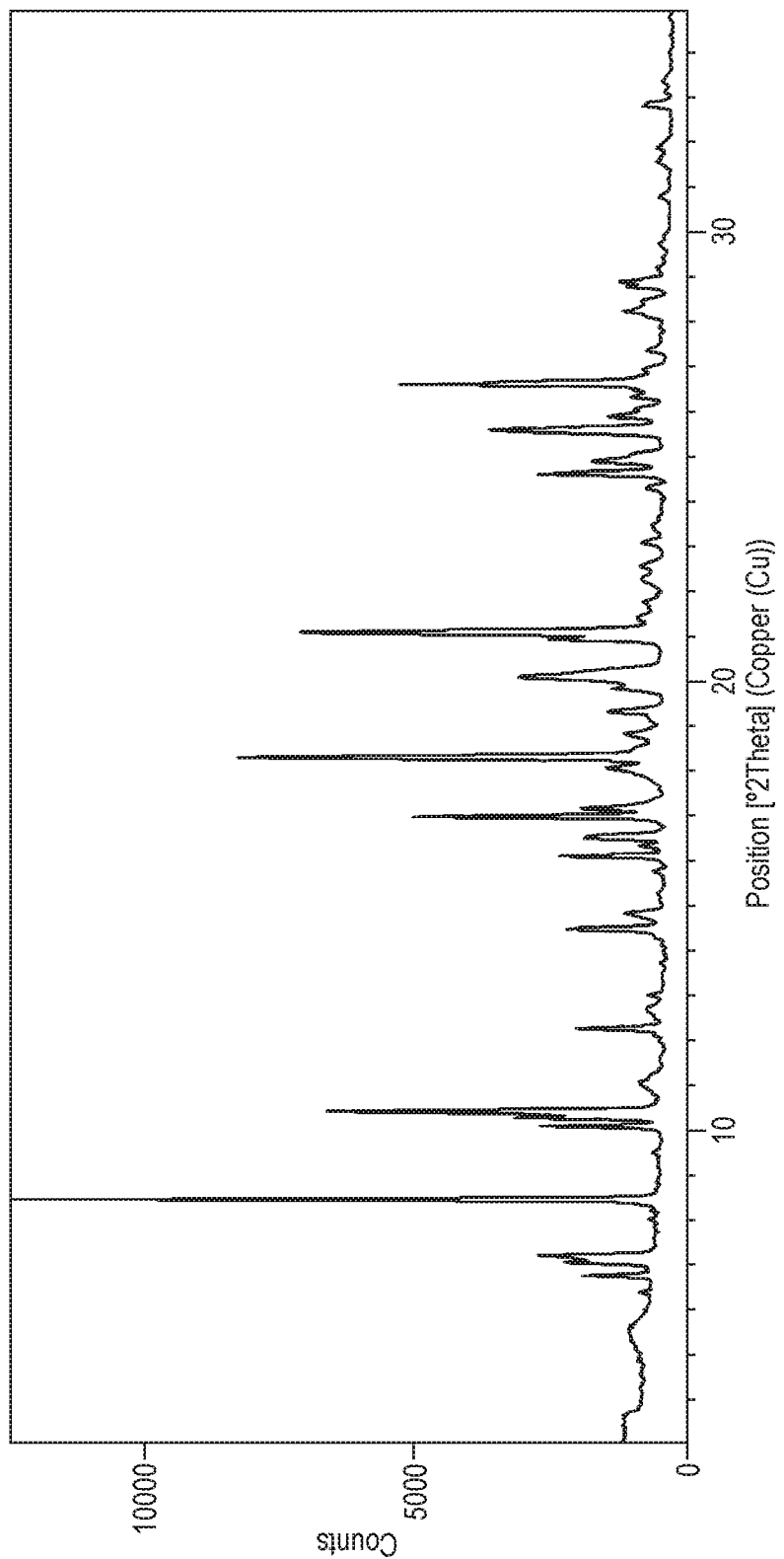
FIG. 1 an X-ray powder diffractogram of the ditosylate salt of N2-(2-ethoxy-4-(4-methyl-4H-1,2,4-triazol-3-yl)phenyl)-6-methyl-N8-neopentylpyrido[3,4-d]pyrimidine-2,8-diamine Form A (° 2 theta).

FIG. 1 shows an XRPD pattern of an embodiment of the invention obtained using the above described method.

In one embodiment, the ditosylate salt of the compound of formula I (Form A) is characterised by a powder XRD pattern comprising two or more peaks selected from 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

In one embodiment, the ditosylate salt of the compound of formula I (Form A) is characterised by a powder XRD pattern comprising three or more peaks selected from 7.2±degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

In another embodiment, the ditosylate salt of the compound of formula I (Form A) is characterised by a powder XRD pattern comprising four or more peaks selected from 7.2±degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

In another embodiment, the ditosylate salt of the compound of formula I (Form A) is characterised by a powder XRD pattern comprising five or more peaks selected from 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

In another embodiment, the ditosylate salt of the compound of formula I (Form A) is characterised by a powder XRD pattern comprising six or more peaks selected from 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

In another embodiment, the ditosylate salt of the compound of formula I (Form A) is characterised by a powder XRD pattern comprising seven or more peaks selected from 7.2±degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

In another embodiment, the ditosylate salt of the compound of formula I (Form A) is characterised by a powder XRD pattern comprising eight or more peaks selected from 7.2±degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

In another embodiment, the ditosylate salt of the compound of formula I (Form A) is characterised by a powder XRD pattern comprising peaks at 7.2±0.2 degrees two-theta, 8.5±0.2 degrees two-theta, 10.4±0.2 degrees two-theta, 12.3±0.2 degrees two-theta, 14.5±degrees two-theta, 16.1±0.2 degrees two-theta, 18.3±0.2 degrees two-theta, 20.1±0.2 degrees two-theta and 21.1±0.2 degrees two-theta.

In another embodiment, the ditosylate salt of the compound of formula I (Form A) is characterised by a powder XRD pattern comprising 1, 2, 3, 4, 5, 6, 7 or 8 peaks selected from 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±degrees two-theta, 20.1±0.2 degrees two-theta and 21.1±0.2 degrees two-theta.

In another embodiment, the ditosylate salt of the compound of formula I (Form A) is characterised by a powder XRD pattern comprising two or more peaks selected from about 7.1±0.2 degrees two-theta, 7.2±0.2 degrees two-theta, 8.5±0.2 degrees two-theta, 10.1±degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising three or more peaks selected from about 7.1±0.2 degrees two-theta, 7.2±0.2 degrees two-theta, 8.5±0.2 degrees two-theta, 10.1±degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising four or more peaks selected from about 7.1±0.2 degrees two-theta, 7.2±0.2 degrees two-theta, 8.5±0.2 degrees two-theta, 10.1±degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising five or more peaks selected from about 7.1±0.2 degrees two-theta, 7.2±0.2 degrees two-theta, 8.5±0.2 degrees two-theta, 10.1±degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising six or more peaks selected from about 7.1±0.2 degrees two-theta, 7.2±0.2 degrees two-theta, 8.5±0.2 degrees two-theta, 10.1±0.2 degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising seven or more peaks selected from about 7.1±0.2 degrees two-theta, 7.2±0.2 degrees two-theta, 8.5±0.2 degrees two-theta, 10.1±degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising eight or more peaks selected from about 7.1±0.2 degrees two-theta, 7.2±0.2 degrees two-theta, 8.5±0.2 degrees two-theta, 10.1±degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising nine or more peaks selected from about 7.1±0.2 degrees two-theta, 7.2±0.2 degrees two-theta, 8.5±0.2 degrees two-theta, 10.1±degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising ten or more peaks selected from about 7.1±0.2 degrees two-theta, 7.2±0.2 degrees two-theta, 8.5±0.2 degrees two-theta, 10.1±degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising 11 or more peaks selected from about 7.1±0.2 degrees two-theta, 7.2±0.2 degrees two-theta, 8.5±0.2 degrees two-theta, 10.1±0.2 degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising 12 or more peaks selected from about 7.1±0.2 degrees two-theta, 7.2±0.2 degrees two-theta, 8.5±0.2 degrees two-theta, 10.1±0.2 degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising 13 or more peaks selected from about 7.1±0.2 degrees two-theta, 7.2±0.2 degrees two-theta, 8.5±0.2 degrees two-theta, 10.1±0.2 degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising 14 or more peaks selected from about 7.1±0.2 degrees two-theta, 7.2±0.2 degrees two-theta, 8.5±0.2 degrees two-theta, 10.1±0.2 degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising 15 or more peaks selected from about 7.1±0.2 degrees two-theta, 7.2±0.2 degrees two-theta, 8.5±0.2 degrees two-theta, 10.1±0.2 degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising peaks selected from about 7.1±0.2 degrees two-theta, 7.2±0.2 degrees two-theta, 8.5±0.2 degrees two-theta, 10.1±0.2 degrees two-theta, 10.3±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern comprising 1, 2, 3, 4, 5, 6, 7, 8, 9, 10, 11, 12, 13, 14 or 15 peaks selected from about 7.1±0.2 degrees two-theta, 7.2±0.2 degrees two-theta, 8.5±0.2 degrees two-theta, 10.1±0.2 degrees two-theta, 10.3±0.2 degrees two-theta, 10.4±degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In one embodiment, the ditosylate salt of the compound of formula I (Form A) is characterised by a powder XRD pattern comprising peaks at about 7.2±0.2 degrees two-theta and 10.4±0.2 degrees two-theta.

In one embodiment, the ditosylate salt of the compound of formula I (Form A) is characterised by a powder XRD pattern comprising peaks at about 7.2±0.2 degrees two-theta, 8.5±0.2 degrees two-theta and 10.4±0.2 degrees two-theta.

In another embodiment, the ditosylate salt of the compound of formula I (Form A) is characterised by a powder XRD pattern comprising peaks at about 7.2±0.2 degrees two-theta, 8.5±0.2 degrees two-theta, 10.4±0.2 degrees two-theta, 18.3±0.2 degrees two-theta, ±0.2 degrees two-theta and 21.1±0.2 degrees two-theta.

In another embodiment, the ditosylate salt of the compound of formula I (Form A) is characterised by a powder XRD pattern comprising peaks at about 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

In another embodiment, the ditosylate salt of the compound of formula I (Form A) is characterised by a powder XRD pattern comprising peaks at about 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta and 21.1±0.2 degrees two-theta.

In another embodiment, the ditosylate salt of the compound of formula I (Form A) is characterised by a powder XRD pattern comprising peaks at about 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 21.1±0.2 degrees two-theta, 25.6±degrees two-theta and 26.6±0.2 degrees two-theta.

In another embodiment, the ditosylate salt of the compound of formula I (Form A) is characterised by a powder XRD pattern comprising peaks at about 7.2±0.2 degrees two-theta, 8.5±0.2 degrees two-theta, 10.1±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 21.1±degrees two-theta, 24.6±0.2 degrees two-theta 25.6±0.2 degrees two-theta and 26.6±degrees two-theta.

In another embodiment, the ditosylate salt of the compound of formula I (Form A) is characterised by a powder XRD pattern comprising peaks at about 7.1±0.2 degrees two-theta, 7.2±0.2 degrees two-theta, 8.5±0.2 degrees two-theta, 10.1±0.2 degrees two-theta, ±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±degrees two-theta, 20.1±0.2 degrees two-theta, 20.9±0.2 degrees two-theta, 21.1±0.2 degrees two-theta, 24.6±0.2 degrees two-theta 25.6±0.2 degrees two-theta and 26.6±0.2 degrees two-theta.

In another embodiment, the ditosylate salt of the compound of formula I (Form A) is characterised by a powder XRD pattern substantially as depicted in FIG. 1.

In one embodiment, the crystalline ditosylate salt of the compound of formula I may be characterised by differential scanning calorimetry (also referred herein as DSC).

Suitably the DSC thermogram may be obtained using a heating rate of about 20° C. per minute (° C.min$^{-1}$), suitably over a range of about 30 to about 350° C. Suitably, the DSC thermograms are acquired under ambient conditions. Suitably the sample is maintained under a dry nitrogen purge during analysis.

In one embodiment, the DSC thermogram is obtainable on a PerkinElmer Pyris 6000 DSC equipped with a 45 position sample holder wherein a predefined amount of the sample, (e.g. about 0.5-3.0 mg), is placed in a pin-holed aluminium pan and heated at about 20° C.min$^{-1}$ from about 30° C. to about 350° C. using a purge of dry nitrogen (about 20 ml min$^{-1}$) over the sample. The instrument control, data acquisition and analysis may be performed with Pyris Software v11.1.1 revision H.

Figure 2:
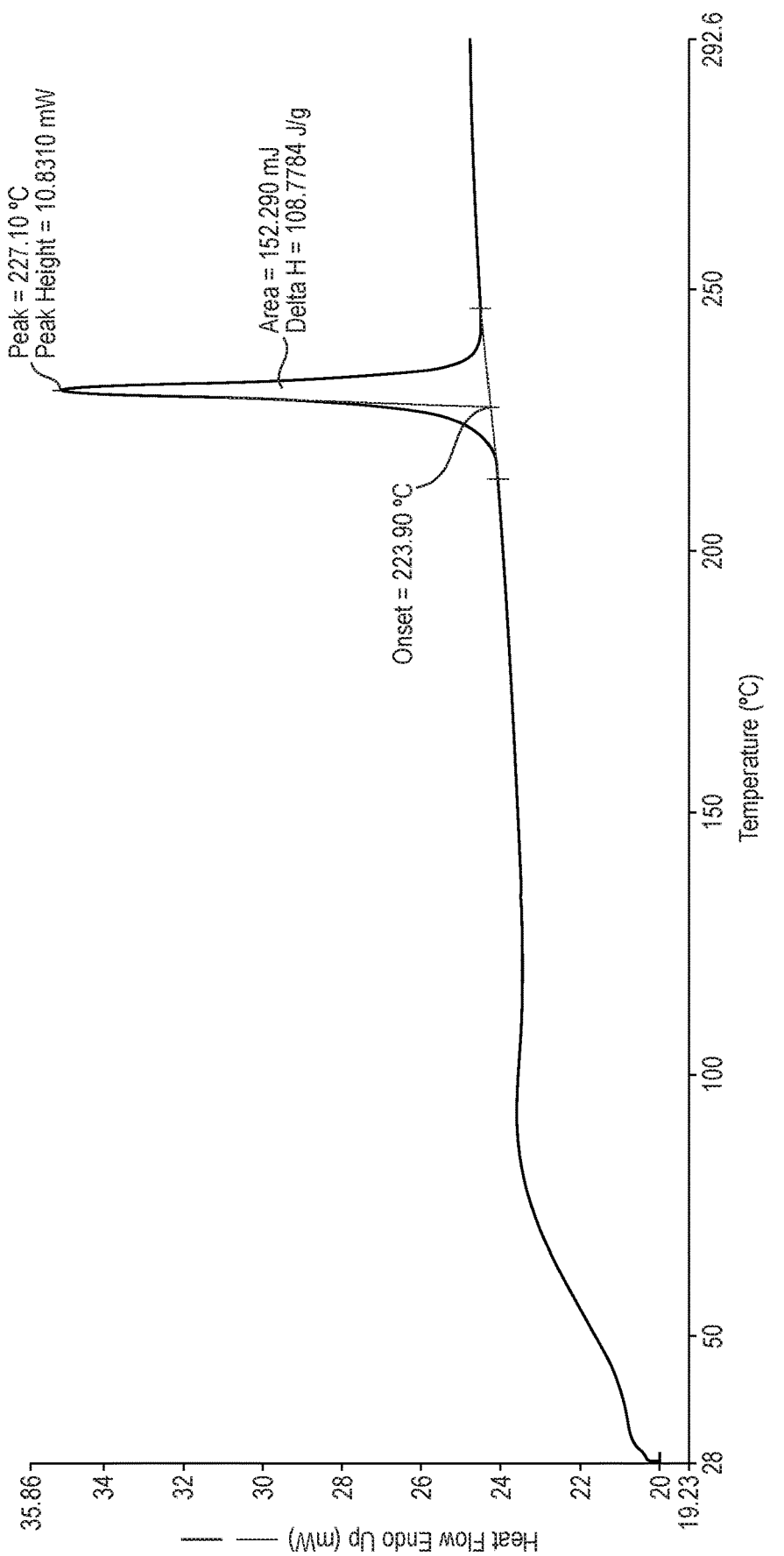
FIG. 2 is a differential scanning calorimetry thermogram of the ditosylate salt of N2-(2-ethoxy-4-(4-methyl-4H-1,2,4-triazol-3-yl)phenyl)-6-methyl-N8-neopentylpyrido[3,4-d]pyrimidine-2,8-diamine Form A.

FIG. 2 shows a DSC thermogram of an embodiment of the invention obtained using the above described method.

In one embodiment, the ditosylate salt of the compound of formula I (Form A) is characterised by a DSC thermogram having an endotherm with onset at about 222 to 228° C., and maximum at about 226 to 230° C.

In another embodiment, the ditosylate salt of the compound of formula I (Form A) is characterised by a DSC thermogram having an endotherm with onset at about 222 to 225° C., and maximum at about 226 to 228° C.

In another embodiment, the ditosylate salt of the compound of formula I (Form A) is characterised by a DSC thermogram substantially as depicted in FIG. 2.

In one embodiment, the ditosylate salt of the compound of formula I (Form A) is characterised by:
(i) a powder XRD pattern comprising peaks at about 7.2±0.2 degrees two-theta and 10.4±0.2 degrees two-theta; and
(ii) a DSC thermogram having an endotherm with onset at about 222 to 228° C., and maximum at about 226 to 230° C.

In another embodiment, the ditosylate salt of the compound of formula I (Form A) is characterised by:
(i) a powder XRD pattern comprising peaks at about 7.2±0.2 degrees two-theta, 8.5±degrees two-theta, 10.4±0.2 degrees two-theta, 18.3±0.2 degrees two-theta, 20.1±0.2 degrees two-theta and 21.1±0.2 degrees two-theta; and
(ii) a DSC thermogram having an endotherm with onset at about 222 to 228° C., and maximum at about 226 to 230° C.

In another embodiment, the ditosylate salt of the compound of formula I (Form A) is characterised by:
(i) a powder XRD pattern comprising peaks at about 7.2±0.2 degrees two-theta, 8.5±degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 21.1±0.2 degrees two-theta, 25.6±0.2 degrees two-theta and 26.6±0.2 degrees two-theta; and
(ii) a DSC thermogram having an endotherm with onset at about 222 to 228° C., and maximum at about 226 to 230° C.

In another embodiment, the ditosylate salt of the compound of formula I (Form A) is characterised by:
(i) a powder XRD pattern comprising peaks at about 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 17.0±0.2 degrees two-theta, 18.3±0.2 degrees two-theta, 20.1±0.2 degrees two-theta, 21.1±0.2 degrees two-theta, 25.6±0.2 degrees two-theta and 26.6±0.2 degrees two-theta; and
(ii) a DSC thermogram having an endotherm with onset at about 222 to 228° C., and maximum at about 226 to 230° C.

Pharmaceutical Compositions

According to a further aspect of the invention there is provided a pharmaceutical composition which comprises a ditosylate salt of the compound of formula I as defined hereinbefore, in association with a pharmaceutically acceptable excipient, diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

Suitably, the composition of the invention is an oral composition.

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative disorder referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutically active agent", whether used alone or in conjunction with another term or terms, refers to any compound, i.e. a drug, that has been found to be useful in the treatment of a disease, disorder or condition and is not described by Formula I. It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

As used herein by themselves or in conjunction with another term or terms, "subject(s)" and "patient(s)", suitably refer to mammals, in particular humans.

In another aspect, the present invention provides a ditosylate salt of a compound of formula I:

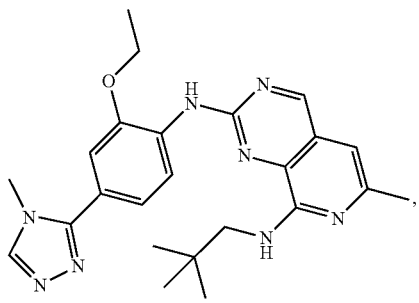

(I)

or a pharmaceutical composition as defined herein, for use in therapy.

The ditosylate salts of the invention are capable of inhibiting MPS1 kinase activity. Thus, in another aspect, the present invention provides a method of inhibiting MPS1 kinase activity in a cell, the method comprising administering to said cell a ditosylate salt of a compound of formula I as defined herein.

In a further aspect, the present invention provides a method of inhibiting MPS1 kinase in vitro or in vivo, said method comprising contacting a cell with an effective amount of a ditosylate salt of a compound of formula I as defined herein.

In another aspect, the present invention provides a method of inhibiting MPS1 kinase activity in a human or animal subject in need of such inhibition, the method comprising administering to said subject an effective amount of a compound of a ditosylate salt of a compound of formula I as defined herein.

In another aspect, the present invention provides a ditosylate salt of a compound of formula I as defined herein for use in the treatment of disease or condition associated with MPS1 kinase activity.

In another aspect, the present invention provides the use of a ditosylate salt of a compound of formula I as defined herein, in the manufacture of a medicament for use in the treatment of disease or condition associated with MPS1 kinase activity.

In yet another aspect, the present invention provides a method of treating a proliferative disorder in a subject, the method comprising administering to said subject a therapeutically acceptable amount of a ditosylate salt of a compound of formula I as defined herein.

In yet another aspect, the present invention provides a ditosylate salt of a compound of formula I as defined herein for use in the treatment of a proliferative disorder.

In yet another aspect, the present invention provides the use of a ditosylate salt of a compound of formula I as defined herein in the manufacture of a medicament for use in the treatment of a proliferative disorder.

The term "proliferative disorder" pertains to an unwanted or uncontrolled cellular proliferation of excessive or abnormal cells which is undesired, such as, neoplastic or hyperplastic growth, whether in vitro or in vivo. Examples of proliferative disorders include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the ditosylate salt of a compound of formula I as defined herein have particular application in the treatment of human cancers by virtue of their MPS1 kinase inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Therefore, in another aspect, the present invention provides a ditosylate salt of a compound of formula I as defined herein, or a pharmaceutical composition as defined herein for use in the treatment of cancer.

In yet another aspect, the present invention provides the use of a ditosylate salt of a compound of formula I as defined herein in the manufacture of a medicament for use in the treatment of cancer.

In yet another aspect, the present invention provides a method of treating cancer in a subject in need of such treatment, said method comprising administering to said subject a therapeutically effective amount of a ditosylate salt of a compound of formula I as defined herein, or a pharmaceutical composition as defined herein.

In one embodiment, the cancer is selected from breast cancer, lung cancer, ovarian cancer, cervical cancer, pancreatic cancer, bladder cancer, esophageal cancer and skin cancer.

In one embodiment, the breast cancer is a triple negative breast cancer or an oestrogen receptor positive breast cancer (ER+).

In another embodiment, the breast cancer is resistant to endocrine therapy; for instance, an endocrine therapy-resistant ER+ breast cancer.

In another embodiment, the breast cancer is resistant to treatment with a CDK4/6 inhibitor; for instance, a CDK4/6 inhibitor-resistant ER+ breast cancer.

In one embodiment, the compounds and compositions of the invention are for use or used in a method of treatment of a human subject wherein said subject has previously been treated with an endocrine therapy; for instance an endocrine agent, such as an aromatase inhibitor (e.g. anastrozole), a selective oestrogen receptor modulator (SERM) (e.g. tamoxifen) and a selective oestrogen receptor degrader/downregulator (SERD) (e.g. fulvestrant).

In another embodiment, the compounds and compositions of the invention are for use or used in a method of treatment of a human subject wherein said subject has previously been treated with a CDK4/6 inhibitor; for instance palbociclib, abemaciclib and ribociclib, or pharmaceutically acceptable salts or solvates thereof.

As used herein "resistant to endocrine therapy" or "endocrine-resistant" cancer may mean said cancer has been determined by a relevant skilled person to be resistant to endocrine therapy. A relevant skilled person would readily be able to determine when a cancer is resistant to endocrine therapy. For instance, clinically, resistance can manifest as relapse or cancer recurrence during or following endocrine therapy. Alternatively, resistance can be observed as clinical progression of primary disease, usually constituting an increase in primary tumour size or disease spread to regional nodes or beyond to more distant metastatic sites. Pathological changes such as increased tumour grade or increased proliferation are indicators of potential resistance to therapy. In the neoadjuvant setting, resistance occurs as either a primary lack of response (no change or an increase in tumour size and no evidence of pathological response) early in treatment, implying innate or de novo resistance, or later following a period of response, suggesting acquired resistance. Alternatively, resistance to endocrine therapy may be determined in endocrine therapy naïve patients by reference to genotypic and/or phenotypic markers of resistance.

As used herein the term "endocrine therapy" refers to any treatment capable of removing oestrogen, blocking generation of oestrogen, reducing levels of oestrogen, blocking the effect of oestrogen, reducing the effect of oestrogen and/or can lead to instability, degradation and/or down regulation of the oestrogen receptor. Suitably, the endocrine therapy comprises/essentially consists of/consists of administration of an endocrine agent.

As used herein, the term "endocrine agent" refers to any chemical compound or biological agent capable of removing oestrogen, blocking generation of oestrogen and/or reducing levels of oestrogen. Suitably, the endocrine agent is a chemical compound, e.g. a drug or a drug-like molecule.

As used herein "resistant to a CDK4/6 inhibitor" or "CDK4/6 inhibitor-resistant" cancer may mean said cancer has been determined by a relevant skilled person to be resistant to a CDK4/6 inhibitor. A relevant skilled person would readily be able to determine when a cancer is resistant to a CDK4/6 inhibitor. For instance, clinically, resistance can manifest as relapse or cancer recurrence during or following treatment with a CDK4/6 inhibitor. Alternatively, resistance can be observed as clinical progression of primary disease, usually constituting an increase in primary tumour size or disease spread to regional nodes or beyond to more distant metastatic sites. Pathological changes such as increased tumour grade or increased proliferation are indicators of potential resistance to therapy. In the neoadjuvant setting, resistance occurs as either a primary lack of response (no change or an increase in tumour size and no evidence of pathological response) early in treatment, implying innate or de novo resistance, or later following a period of response, suggesting acquired resistance. Alternatively, resistance to a CDK4/6 inhibitor may be determined in CDK4/6 inhibitor-naïve patients by reference to genotypic and/or phenotypic markers of resistance.

As used herein, the term CDK4/6 inhibitor refers to chemical or biological agents capable of inhibiting CDK4 and CDK6. Suitably, the CDK4/6 inhibitors are selective for CDK 4 and 6 over other kinases, particularly over other CDKs.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Process for Preparation of the Ditosylate Salt

In one aspect, the present invention relates to a process for the preparation of a ditosylate salt of a compound of formula I

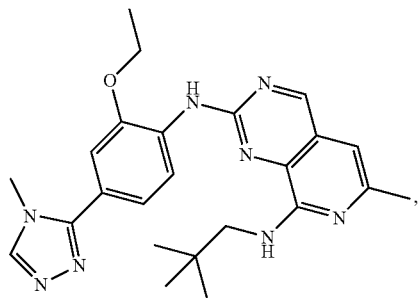

(I)

comprising preparing a mixture of para-toluenesulfonic acid and a compound of formula I in an organic solvent and water, wherein the organic solvent is selected from acetone, 2-butanone and 2-propanol.

Suitably, at least two equivalents of para-toluenesulfonic acid is used for every equivalent of compound of formula I.

Suitably, the ratio of organic solvent to water is about 5:1 to 15:1. Suitably about 6:1 to 13:1.

In one embodiment, the compound of formula I is first suspended in an organic solvent consisting of acetone, 2-butanone or 2-propanol, and optionally water. Suitably this suspension is heated so as to dissolve the compound of formula I. Suitably the suspension is heated to between about 50° C. to about 80° C. In one embodiment, the para-toluenesulfonic acid is added to the afore-mentioned suspension/solution of the compound of formula I. Suitably, the para-toluenesulfonic acid is added in the form of an aqueous solution or a solution comprising a mixture of water and an organic solvent selected from acetone, 2-butanone and 2-propanol. Suitably, the organic solvent in which the compound of formula I and the para-toluenesulfonic acid are dissolved/suspended are the same.

In one embodiment, the process comprises:
(a) suspending the compound of formula I in a solution comprising an organic solvent selected from acetone, 2-butanone and 2-propanol;
(b) heating the product of step (a) to between about 50 to about 80° C.;
(c) mixing the product of step (b) with para-toluenesulfonic acid; and
(d) cooling the product of step (c).

In one embodiment, in step (a), the compound of formula is suspended in a solution consisting of acetone, 2-butanone or 2-propanol. Suitably, consisting of 2-propanol.

In one embodiment, in step (c) the para-toluenesulfonic acid is added to the product of step (b) as an aqueous solution.

In one embodiment, in step (d) the product is cooled to between about 0° C. and about 40° C. in order to yield the ditosylate salt of the compound of formula I as a precipitate. The precipitate can then be isolated and dried using techniques known in the art such as filtration.

In one embodiment, the process comprises:
(a') suspending the compound of formula I in a solution consisting of 2-propanol;
(b') heating the product of step (a') to between about 60 to about 75° C.;
(c') mixing the product of step (b') with an aqueous solution of para-toluenesulfonic acid; and
(d') cooling the product of step (c') to between 0° C. and about 40° C. in order to yield the ditosylate salt of the compound of formula I.

Suitably, the ratio of 2-propanol to water in step (c') is between about 9:1 to about 13:1.

Suitably, at least two equivalents of para-toluenesulfonic acid, relative to the compound of formula I, are used in step (c) or (c'). Suitably between about 2 and about 2.5 equivalents, more suitably about 2.25 equivalents.

In another aspect, the present invention relates to a ditosylate salt of the compound of formula I obtained/obtainable according to the above described processes or an embodiment thereof.

EXAMPLES

The following examples are provided solely to illustrate the present invention and are not intended to limit the scope of the invention, as described herein.

The compounds of formula I may be prepared using synthetic techniques that are known in the art and, in particular, using the method as described in WO 2014/037750 which is incorporated herein by reference.

Instruments and Methods
1. Solution Proton NMR $^1$H NMR spectra were collected using a JEOL ECX 400 MHz spectrometer equipped with an auto-sampler. The samples were dissolved in a suitable deuterated solvent for analysis. The data were acquired using Delta NMR Processing and Control Software version 4.3.

2. X-Ray Powder Diffraction (XRPD)

X-Ray Powder Diffraction patterns were collected on a PANalytical diffractometer using Cu Kα radiation (45 kV, 40 mA), 6-6 goniometer, focusing mirror, divergence slit (½"), soller slits at both incident and divergent beam (4 mm) and a PIXcel detector. The software used for data collection was X'Pert Data Collector, version 2.2f and the data were presented using X'Pert Data Viewer, version 1.2d.

XRPD patterns were acquired under ambient conditions via a transmission foil sample stage (polyimide—Kapton, 12.7 μm thickness film) under ambient conditions using a PANalytical X'Pert PRO. The data collection range was 2.994-35° 2θ with a continuous scan speed of 0.202004° s$^{-1}$.

3. Differential Scanning Calorimetry (DSC)

DSC data were collected on a PerkinElmer Pyris 6000 DSC equipped with a 45 position sample holder. The instrument was verified for energy and temperature calibration using certified indium. A predefined amount of the sample, 0.5-3.0 mg, was placed in a pin-holed aluminium pan and heated at 20° C.min$^{-1}$ from 30 to 350° C., or varied as experimentation dictated. A purge of dry nitrogen at 20 ml min$^{-1}$ was maintained over the sample. The instrument control, data acquisition and analysis was performed with Pyris Software v11.1.1 revision H.

4. Low pH LC/MS Method
HPLC Conditions:
System: Agilent1100 series liquid chromatograph or equivalent
Column: Acquity BEH Phenyl 4.6×30 mm; 1.7 μm particle size
(Ex. Waters #186004644)
Mobile phase A: Water:TFA (100:0.03)
Mobile phase B: Acetonitrile:TFA (100:0.03)
Flow rate: 2.0 ml.min$^{-1}$
Injection volume: 5 μl
Detection: UV detection (Default 254 nm, wavelength project dependent)
Column temp.: 40° C.
Post run: 2.3 mins
Gradient:

| Time (mins) | % A | % B |
| --- | --- | --- |
| 0 | 95 | 5 |
| 5.2 | 5 | 95 |
| 5.7 | 5 | 95 |
| 5.8 | 95 | 5 |
| 6.2 | 95 | 5 |

Mass Spec Conditions:
System: Bruker Esquire 3000 Plus Ion Trap MS
Ion Polarity: Positive
Ion Source: Type ESI
Nebuliser: 50 psi
Dry Gas: 10 l/min
Dry Temperature: 350° C.
Target Mass: 400 m/z
Scan Range: 50 m/z-1000 m/z
Sample Preparation:
Sample preparation is approximately 0.25 mg·ml$^{-1}$ in MeCN:Water (1:1), using sonication to fully dissolve sample.

Synthesis and Characterisation
Preparation 1 of Ditosylate Salt of the Compound of Formula I In a 10 L flask under nitrogen, the compound of formula I as the free base (463 g) was suspended in 2-propanol (3936 mL). The suspension was heated to 75° C. and added with a solution p-toluenesulfonic acid monohydrate (447.4 g) dissolved in 2-propanol (347 mL) and water (347 mL) over 20 mins maintaining a ΔT less than 5° C. During the addition, the slurry became a solution. The solution was stirred for 10 minutes, then clarified via an inline capsule filter, Amazon Filters SupaPore 16PCG/16PGG, 1.2 microns, into a pre-heated (75° C.) flask via nitrogen push. The mixture was then cooled to ambient temperature over approximately 6 hours. Crystallisation began at approximately 40° C. The slurry was stirred overnight at ambient temperature and then cooled to 0° C. and stirred for 2 hours. The solids were filtered off, washed with 2-propanol (2×926 mL) and then dried under vacuum at 50° C. for 72 hours.

This yielded the ditosylate salt, 657 g (80.1% yield), as a dark yellow highly crystalline powder, free from visible contamination.

Figure 3:
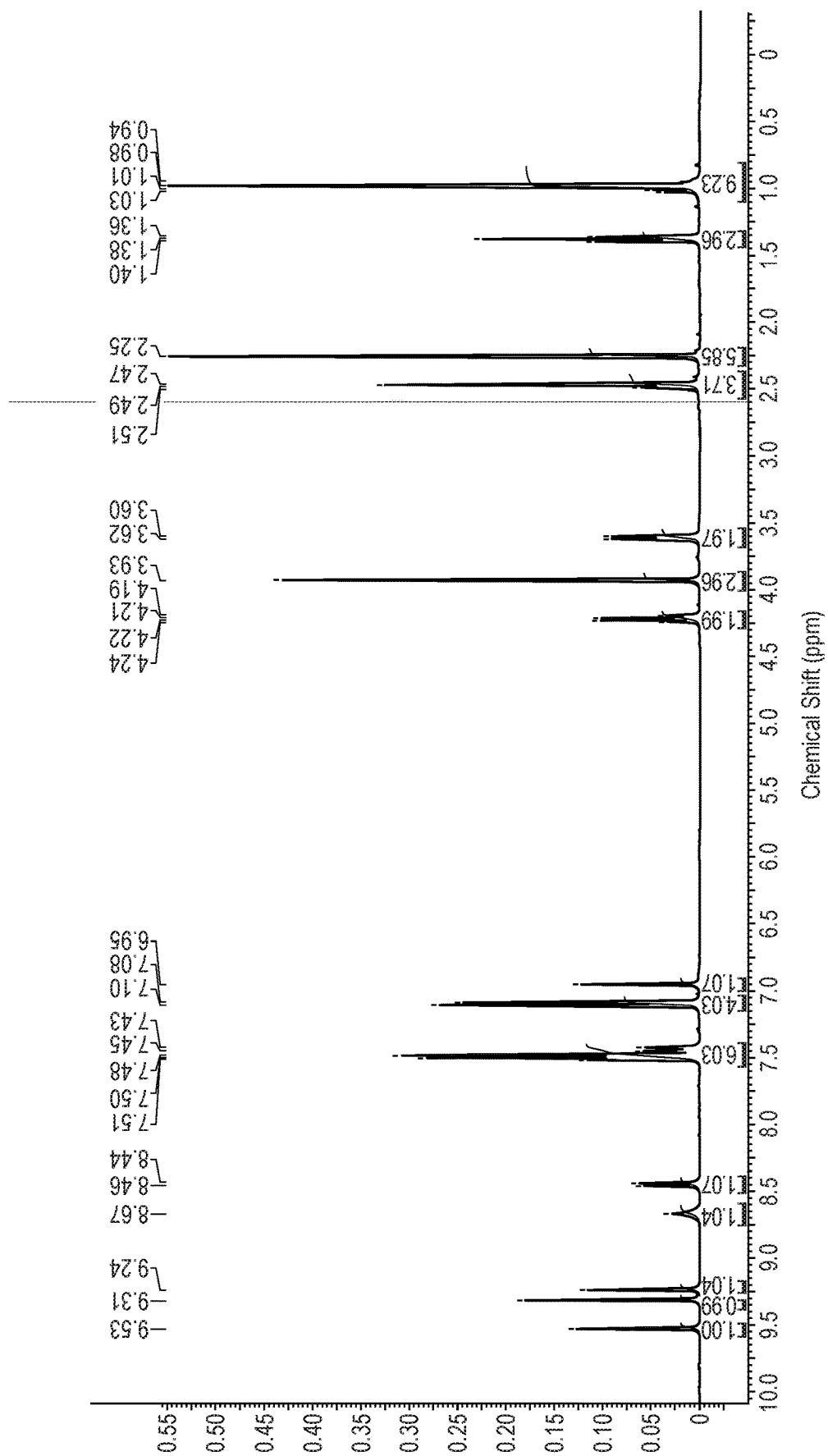
FIG. 3 is a ¹H-NMR spectrum of the ditosylate salt of N2-(2-ethoxy-4-(4-methyl-4H-1,2,4-triazol-3-yl)phenyl)-6-methyl-N8-neopentylpyrido[3,4-d]pyrimidine-2,8-diamine.

XRPD analysis and DSC is concordant with Form A (see FIGS. 1 and 2). $^1$H-NMR (400 MHZ, MeOD) is consistent with the ditosylate salt of the compound of formula I (see FIG. 3).

Preparation 2 of Ditosylate Salt of the Compound of Formula I

The compound of formula I as the free base (2.0 g) was suspended in 2-propanol (65.5 ml, 32.75 vols) and heated to ca 70° C. p-Toluenesulfonic acid monohydrate (1.7034 g, 2 equivalents) in deionised water (5.16 ml, 2.6 vols) was charged slowly to the yellow suspension. Dissolution of the solid, to a dark brown solution, was observed following the addition of a third to half of the p-toluenesulfonic acid solution. Upon complete addition, the solution was clarified through a large nylon syringe filter (0.44 µm) into a pre-heated vessel and the solution returned to 70° C. The solution was cooled to 40° C. over about 1.5 hours and then held at this temperature for ca 1 hour. The mixture was cooled to 30° C. and held at this temperature for ca 2 hours. Crystallisation was observed at ca 44° C. and the extent of crystallisation increased during the hold period at 40° C. The mixture was then cooled to and maintained at ambient temperature for ca 16 hours. The yellow suspension was then cooled to 0-4° C. and held at this temperature for 1 hour. The solid was isolated by filtration under vacuum and the flask residue was rinsed with 2-propanol (2×2 ml) and used to wash the filter cake. The solid was allowed to air dried under vacuum for 20 minutes and then dried in vacuo at 50° C. for ca 2.5 hours to afford the ditosylate salt of the compound of formula I as a yellow solid (2.62 g, 74.21% yield).

XRPD analysis and DSC is concordant with Form A (see FIGS. 1 and 2). $^1$H-NMR (400 MHZ, MeOD) is consistent with the ditosylate salt of the compound of formula I (see FIG. 3).

Assessment of the Solubility of the Ditosylate Salt of the Compound of Formula I in a Range of Dissolution Media Crystalline ditosylate salt of the compound of formula I (about 40 mg, Form A) was suspended by gentle shaking in various aqueous buffers, biologically relevant media and formulation vehicles, 2×0.5 ml, at ambient temperature, ca 20° C. The mixtures were then heated to 37° C. with agitation for a minimum of 23 hours. The pH of the aqueous mixtures were also measured.

Table 1 presents the pH measurements and the solubility in various dissolution media.

TABLE 1

| Dissolution medium | pH | Solubility (mg/ml) |
|---|---|---|
| Water, deionised | 2.13 | 5.85 |
| Acetate buffer | 4.33 | 0 |
| Phosphate buffer | 2.56 | 2.24 |
| Sodium chloride 0.9% w/v | 2.01 | 9.58 |
| NaCl,0.9%/DMSO/Tween 20 | 1.97 | 12.69 |
| PEG300 | Not recorded | 2.90 |
| FeSSIF | 3.05 | 1.69 |
| FaSSIF | 2.41 | 14.21 |
| SFaGF | 1.40 | 5.72 |

Stability Assessment of the Ditosylate Salt after Storage at 40° C. and 75% RH for 3 Weeks The ditosylate salt of the compound of formula I was stored at 40° C. and 75% RH in loose screw top vials for 3 weeks.

Figure 4:
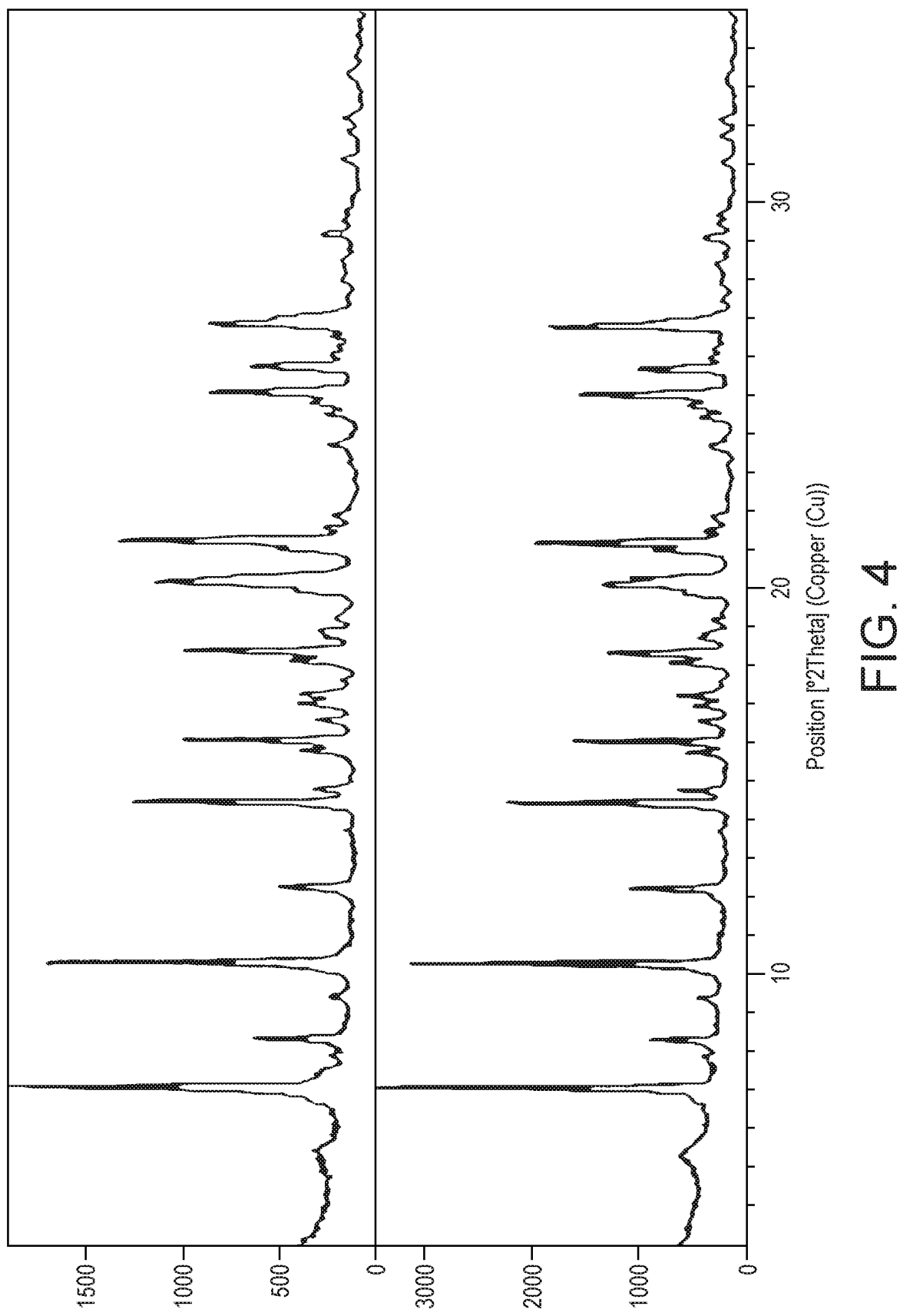
FIG. 4 compares the XRPD of the ditosylate before (top) and after (bottom) storage at 40° C. and 75% RH.

No change in appearance of the ditosylate salt was observed and it remained a free flowing solid. Furthermore, there was no evidence of chemical degradation. FIG. 4 compares the XRPD of the ditosylate before (top) and after (bottom) storage at 40° C. and 75% RH. No evidence of form modification is observed.

Dynamic Vapour Sorption (DVS) Assessment of the Ditosylate Salt

The ability of samples studied to absorb moisture (or not) over a set of well-determined humidity ranges was assessed.

Sorption isotherms were obtained using a Hiden Isochema moisture sorption analyser (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 ml·min$^{-1}$. The instrument was verified for relative humidity content by measuring three calibrated Rotronic salt solutions (10-50-88%). The weight change of the sample was monitored as a function of humidity by a microbalance (accuracy +/-0.005 mg). A defined amount of sample (typically 10-15 mg powder) was placed in a tared mesh stainless steel basket under ambient conditions. A full experimental cycle typically consisted of three scans (desorption, sorption, and desorption) at a constant temperature (25° C.) and 10% RH intervals over a 0-90% range (60 minutes for each humidity level).

Solids are then held post cycle at 0% RH for 2-3 hours and tested by XRPD and the remainder held at 90% RH for 2-3 hours and re-tested by XRPD.

Figure 5:
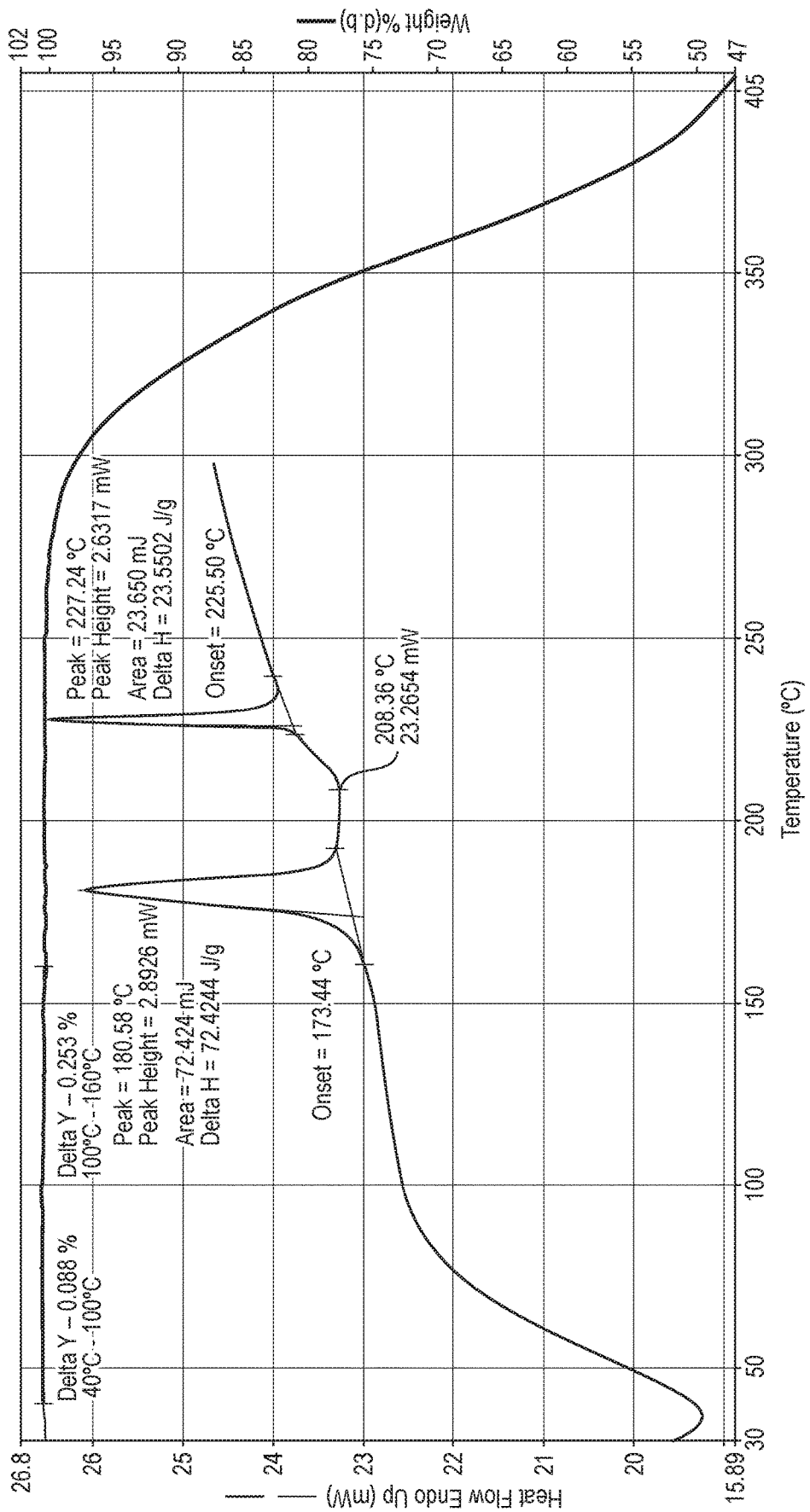
FIG. 5 is a differential scanning calorimetry thermogram of the ditosylate salt of N2-(2-ethoxy-4-(4-methyl-4H-1,2,4-triazol-3-yl)phenyl)-6-methyl-N8-neopentylpyrido[3,4-d]pyrimidine-2,8-diamine Form C.
Figure 7:
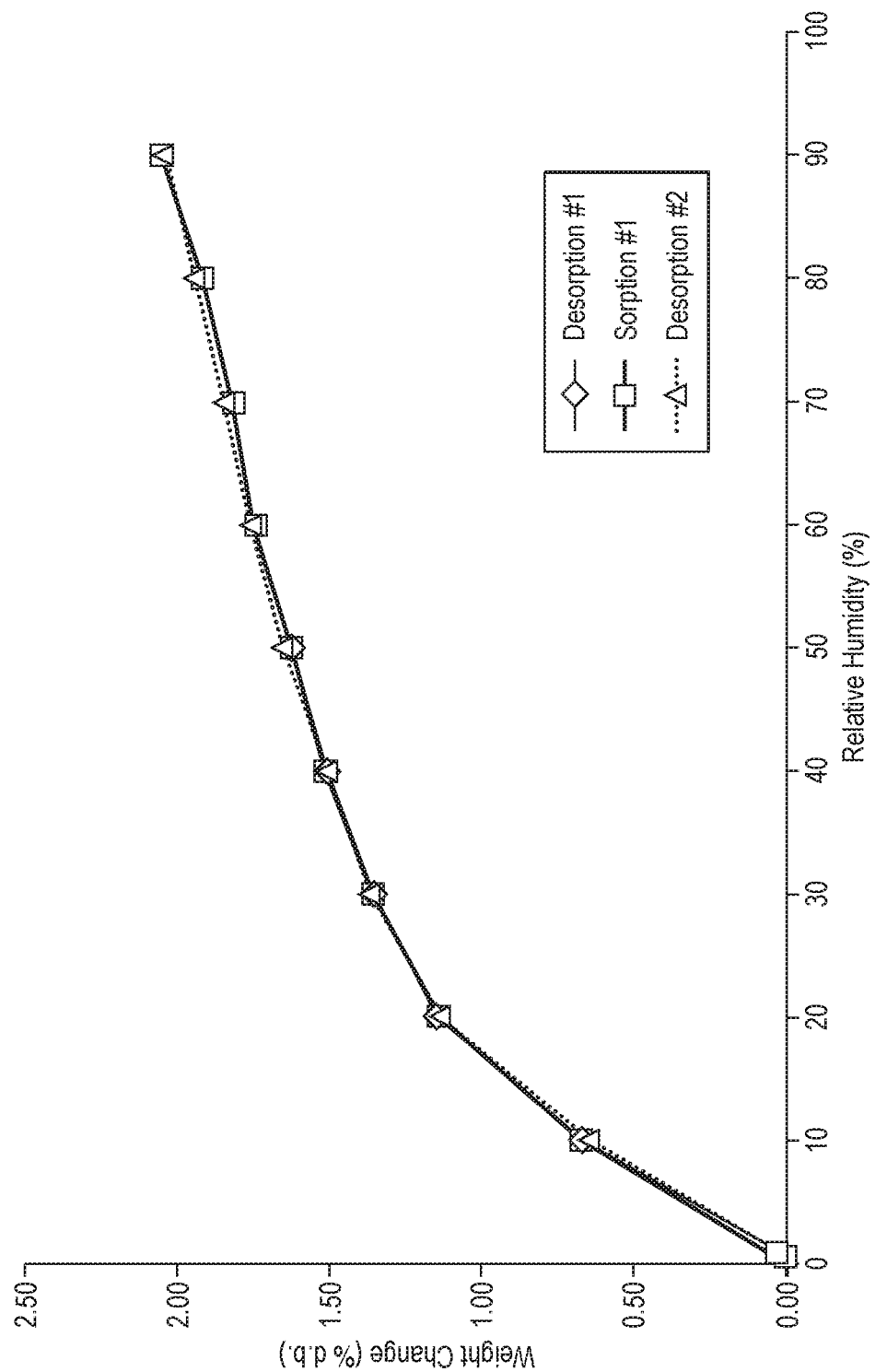
FIG. 7 shows the DVS profile of the ditosylate salt of N2-(2-ethoxy-4-(4-methyl-4H-1,2,4-triazol-3-yl)phenyl)-6-methyl-N8-neopentylpyrido[3,4-d]pyrimidine-2,8-diamine Form A.
Figure 8:
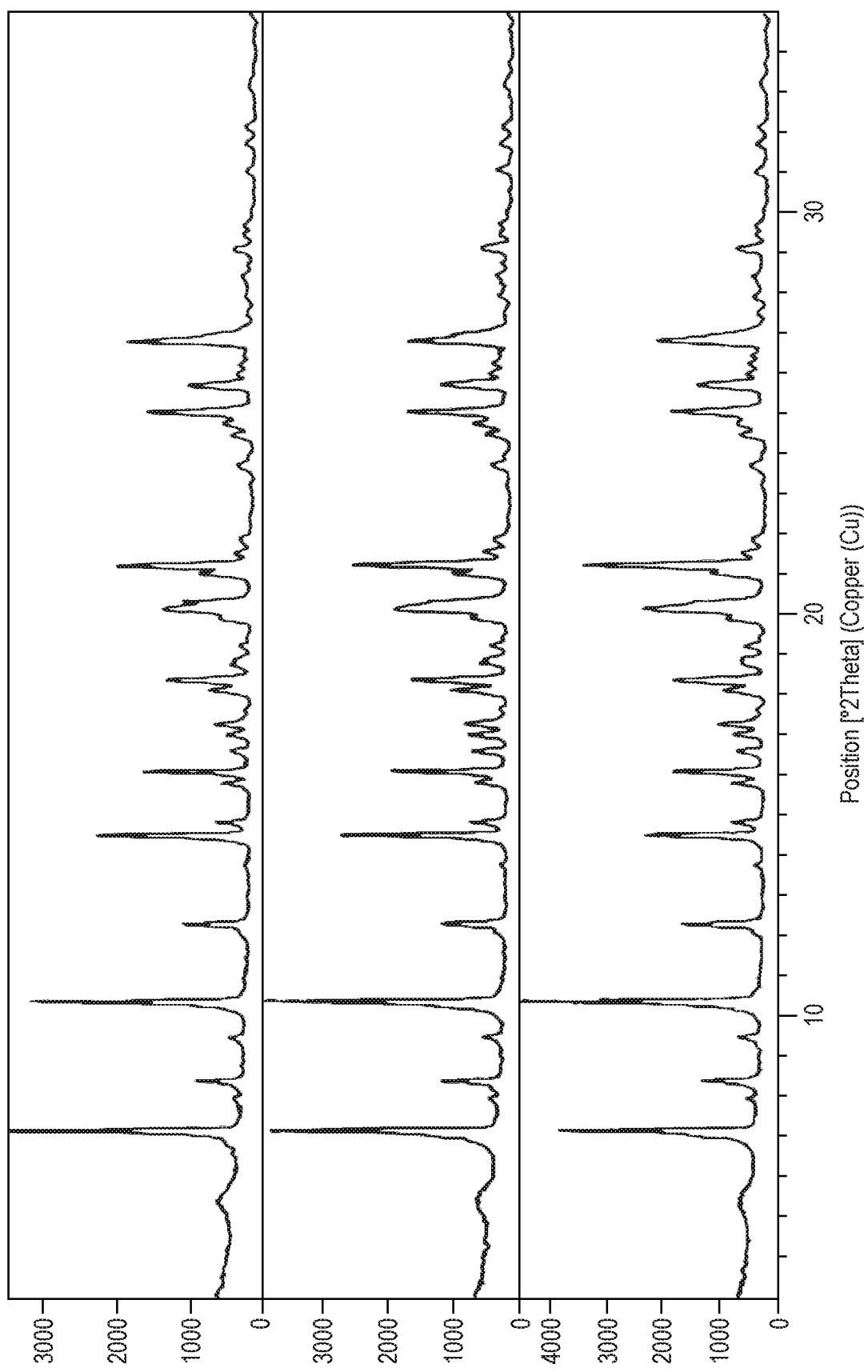
FIG. 8 compares the XRPD of the ditosylate salt of N2-(2-ethoxy-4-(4-methyl-4H-1,2,4-triazol-3-yl)phenyl)-6-methyl-N8-neopentyl pyrido[3,4-d]pyrimidine-2,8-diamine Form A pre DVS analysis (top), post DVS analysis (i.e. 0% RH) (middle) and during DVS analysis at the extreme of humidity (i.e. 90% RH) (bottom).

The DVS profile, FIG. 7, of the ditosylate salt (Form A) revealed reversible water uptake over the humidity range and no hysteresis. The water uptake/loss from 0 to 90% was gradual and equated to about 1.0 equivalents of water at 2.13%. Conditional storage of the ditosylate salt was not considered to be required since the solid post DVS and exposure to 90% RH was free flowing during manipulation. The XRPD patterns, FIG. 8, of the ditosylate salt post DVS (FIG. 8, middle) and at the extremes of humidity (see FIG. 5, bottom) revealed no evidence of form change. The recorded water uptake and loss did not appear to alter the form of the salt.

The ditosylate salt has attractive physiochemical properties as identified in the solubility and stability studies. There is no evidence of appearance change, chemical degradation, form change or hydration of the ditosylate salt following storage at 40° C. and 75% RH for 3 weeks. The ditosylate salt displayed superior behaviour to humidity during DVA analysis.

Recrystallisation Studies

The ditosylate salt of the compound of formula I (about 100 mg) was suspended in a designated volume of water miscible solvent at a given temperature, followed by the addition of one volume aliquots of pre-heated water until dissolution was achieved. The agitated mixtures were then cooled to 20° C. and agitated for about 16 hours. The solids were isolated by filtration and dried in vacuo at 50° C. Solvent, solvent ratios and form classification of the isolated solids are detailed in Table 2.

TABLE 2

| Solvent | Volumes of solvent | Volumes of water | Temp (° C.) | XRPD Observations |
|---|---|---|---|---|
| Ethanol | 15 | — | 80 | Form C |
| Ethanol | 2 | 1 | 60 | Form A |
| Acetone | 10 | 2 | 60 | Form A |
| 2-propanol | 8 | 1 | 80 | Form A |
| Acetonitrile | 2 | 1 | 60 | Form A |
| 2-butanone | 8 | 1 | 80 | Form A |

The ditosylate salt isolated from exclusively ethanol returned an XRPD pattern different to all other conditions. The $^1$H-NMR spectrum of this version of ditosylate salt showed that no salt disproportionation had taken place, nor the presence of any residual ethanol. The chemical purity by HPLC-MS was 99.0% which confirmed that chemical integrity had been maintained.

DSC thermograph of this version of the ditosylate salt (FIG. 5) exhibited a broad endotherm with an onset at ca. 173.4° C. and maximum at 180.6° C. then a minor exotherm at about 208° C. followed by a sharper endotherm with an onset at about 225.5° C. and maximum at about 227.4° C. which corresponded to the melting of ditosylate Form A.

Figure 6:
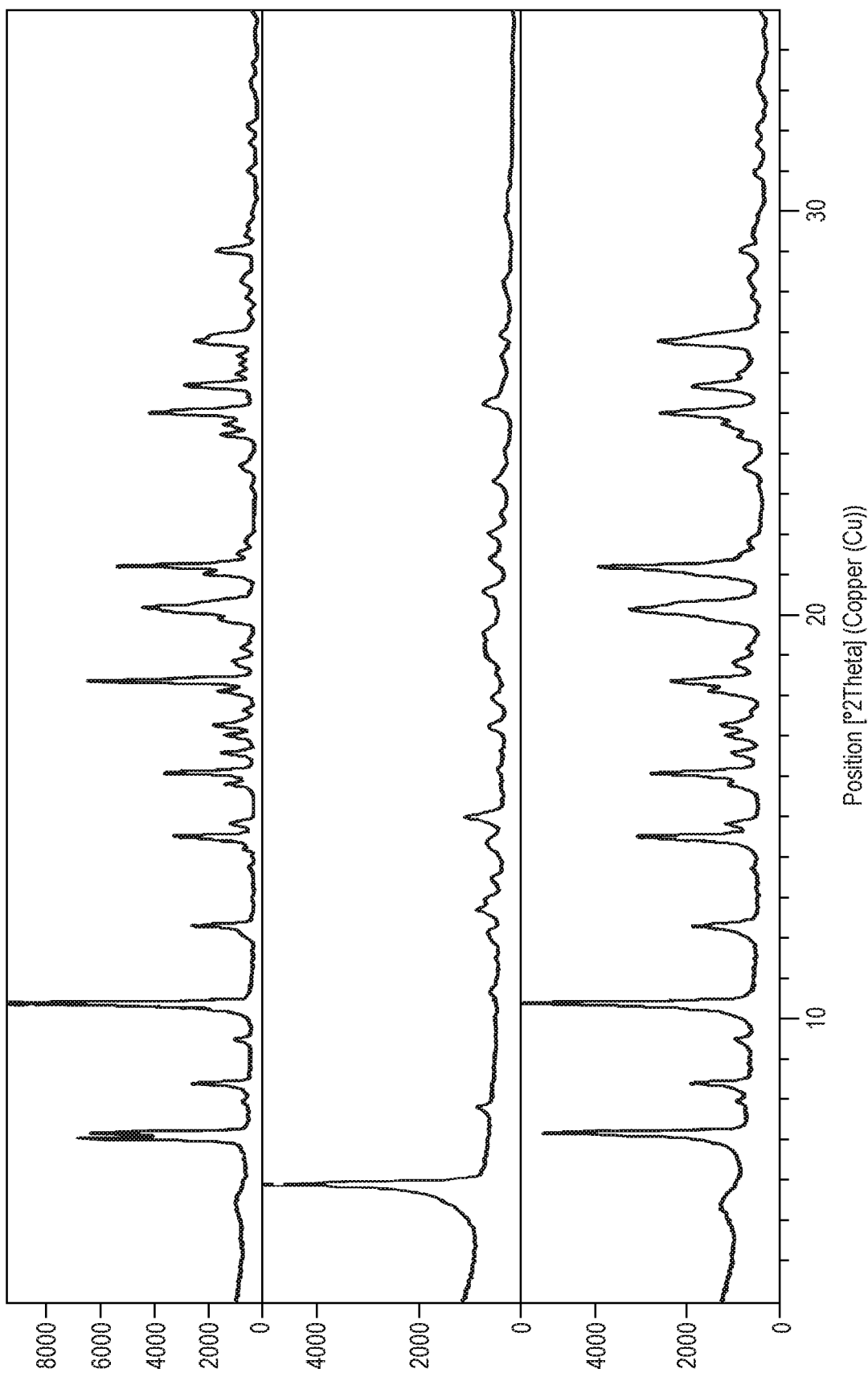
FIG. 6 compares the XPRD patterns of the ditosylate salt Form A (top) versus the ditosylate Form C pre-thermal manipulation (middle) and post-thermal manipulation (bottom).

The XRPD pattern (FIG. 6) of the solid post thermal manipulation was concordant with ditosylate Form A. This revealed that the ditosylate Form C was a metastable form that could be thermally converted to ditosylate Form A. Consequently, it is very likely that Form C is a less stable polymorph of the ditosylate of compound of formula I.

Investigation of the Propensities of the Ditosylate Salt to Polymorphism by Solvent Mediated Equilibrium The equilibration of a solid in various solvents with temperature modulation is an accepted approach to investigate the form stability of a solid and the generation of alternate modifications, polymorphs/solvates of the material.

The ditosylate of the compound of formula I, 35 mg, was subjected to equilibration in various solvents with agitation at 20° C. for 90 hours, 40° C. for 3 hours, cooled to 20° C. over 3 hours, then heated to 40° C. for 16 hours and cooled to 20° C. The solvents were initially charged to the salts in aliquots, 0.25 ml, until dissolution was observed or a volume of 2 ml achieved. The solids were isolated by filtration and dried in vacuo at 50° C. for about 16 hours and then analysed by XRPD.

The solvents employed and form classification by XRPD of the isolated solids are detailed in Table 3.

TABLE 3

| Solvent System | XRPD classification |
| --- | --- |
| Methanol | Form A |
| 2-Propanol | Form A |
| 1-Butanol | Form A |
| 3-Methyl-1-butanol | Form A |
| TBME | Form A |
| 2-Methyltetrahydrofuran | Form A |
| 1,4-Dioxane | Form A |
| Ethyl acetate | Form A |
| Isopropyl acetate | Form A |
| n-Butyl acetate | Form A |
| Methyl isobutyl ketone | Form A |
| Toluene | Form A |
| Chlorobenzene | Form A |
| Trifluorotoluene | Form A |
| Heptane | Form A |
| Methylcyclohexane | Form A |
| 2-Chlorobutane | Form A |
| Acetonitrile | Form A |
| Nitromethane | Form A |
| Water | Form A |

The ditosylate salt demonstrated a remarkable lack of propensity to exhibit version or polymorphic variance. With the exception of metastable, Form C, no other versions were identified in these studies other than thermodynamically preferred Form A.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

The invention claimed is:

1. A ditosylate salt of a compound of formula I:

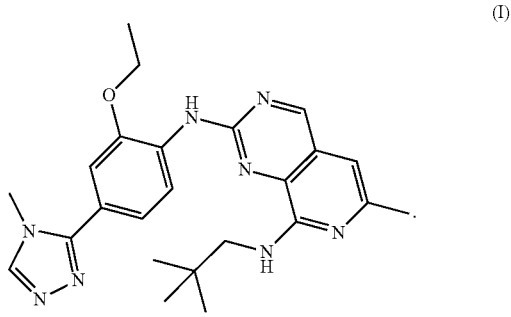 [SMILES: CCOc1cc(-c2nncn2C)ccc1Nc1ncc2cc(C)nc(NCC(C)(C)C)c2n1]

(I)

2. The ditosylate salt of the compound of formula I of claim 1, wherein the ditosylate salt is in a crystalline form.

3. The ditosylate salt of the compound of formula I of claim 2, wherein the ditosylate salt is in crystalline Form A.

4. The ditosylate salt of the compound of formula I of claim 2, wherein the ditosylate salt is characterised by a powder XRD pattern comprising two or more peaks selected from 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

5. The ditosylate salt of the compound of formula I of claim 2, wherein the ditosylate salt is characterised by a powder XRD pattern with peaks at about 7.2±0.2 degrees two-theta and 10.4±0.2 degrees two-theta.

6. The ditosylate salt of the compound of formula I of claim 2, wherein the ditosylate salt is characterised by a powder XRD pattern with peaks at about 7.2±0.2 degrees two-theta, 8.5±0.2 degrees two-theta, 10.4±0.2 degrees two-theta, 18.3±0.2 degrees two-theta, 20.1±0.2 degrees two-theta and 21.1±0.2 degrees two-theta.

7. The ditosylate salt of the compound of formula I of claim 2, wherein the ditosylate salt is characterised by a powder XRD pattern with peaks at about 7.2±0.2 degrees two-theta, 8.5±0.2 degrees two-theta, 10.4±0.2 degrees two-theta, 12.3±0.2 degrees two-theta, 14.5±0.2 degrees two-theta, 16.1±0.2 degrees two-theta, 18.3±0.2 degrees two-theta, 20.1±0.2 degrees two-theta and 21.1±0.2 degrees two-theta.

8. The ditosylate salt of the compound of formula I of claim 2, wherein the ditosylate salt is characterised by a powder XRD pattern substantially as depicted in FIG. 1.

9. The ditosylate salt of the compound of formula I of claim 2, wherein the ditosylate salt is characterised by a DSC thermogram having an endotherm with onset at about 222° C. to about 228° C., and maximum at about 226° C. to about 230° C.

10. The ditosylate salt of the compound of formula I of claim 2, wherein the ditosylate salt is characterised by a DSC thermogram substantially as depicted in FIG. 2.

11. A pharmaceutical composition comprising the ditosylate salt of the compound of formula I of claim 1 and a pharmaceutically acceptable excipient.

12. A method of treating a proliferative disorder, comprising administering to a subject in need thereof the ditosylate salt of the compound of formula I of claim 1.

13. The method of claim 12, wherein the proliferative disorder is a cancer.

14. The method of claim 13, wherein the cancer is selected from breast cancer, lung cancer, ovarian cancer, cervical cancer, pancreatic cancer, bladder cancer, esophageal cancer and skin cancer.

15. A process for the preparation of the ditosylate salt of the compound of formula I of claim 1, comprising preparing a mixture of para-toluenesulfonic acid and the compound of formula I in an organic solvent and water, wherein the organic solvent is selected from acetone, 2-butanone and 2-propanol.

16. The process of claim 15, comprising:
(a') suspending the compound of formula I in a solution consisting of 2-propanol;
(b') heating the product of step (a') to between about 60 to about 75° C.;
(c') mixing the product of step (b') with an aqueous solution of para-toluenesulfonic acid; and
(d') cooling the product of step (c') to between 0° C. and about 40° C. in order to yield the ditosylate salt of the compound of formula I.

17. The process of claim 16, wherein the ratio of 2-propanol to water in step (c') is between about 9:1 to about 13:1.

\* \* \* \* \*